United States Patent [19]

Whyte

[11] 4,339,356

[45] Jul. 13, 1982

[54] HEAVILY PERFUMED PARTICLES

[75] Inventor: David D. Whyte, Cincinnati, Ohio

[73] Assignee: The Procter & Gamble Company, Cincinnati, Ohio

[21] Appl. No.: 221,873

[22] Filed: Dec. 31, 1980

[51] Int. Cl.³ .......................... C11B 9/00; A61K 7/46
[52] U.S. Cl. ............................ 252/522 A; 252/522 R; 252/174.11
[58] Field of Search ....................... 252/522 A, 522 R

[56] References Cited

U.S. PATENT DOCUMENTS 3,804,796  4/1974  Alexandre ..................... 252/522 A

*Primary Examiner*—John F. Niebling
*Attorney, Agent, or Firm*—Michael J. Roth; Eric W. Guttag; Richard C. Witte

[57] ABSTRACT

Heavily perfumed detergent compositions having both immediate and long lasting perfume emitting properties are prepared by a process in which perfume is emulsified in a water solution of water-soluble polymer, and the emulsion is mixed with a powdered hydratable material, in such a ratio that all of the water in the emulsion can be bound in the resulting hydrate, eliminating a separate drying step. The result is a dry, free flowing granular material which can be readily dry mixed into fully formulated detergent compositions. The perfume is retained in the polymeric matrix and is released at the point of product use when contacted with water.

12 Claims, No Drawings

HEAVILY PERFUMED PARTICLES

TECHNICAL FIELD

This invention relates to heavily perfumed particles and their use in detergent compositions. More particularly it relates to perfume particles having both immediate and long lasting perfume emitting properties.

The use of perfume in various consumer products for aestnetic reasons is well known. Detergent compositions in particular generally contain a perfume. The perfume is normally simply admixed with the remainder of the detergent composition, whether it is a liquid or solid detergent composition. While the perfume does not add to cleaning performance, it does make the product more aesthetically pleasing to the consumer, and, in some cases, imparts a pleasant fragrance to treated articles or surfaces. The consumer has come to expect such detergent products to have a pleasing odor.

Perfumes are, by their nature, made of a combination of volatile substances. Because of this, the perfume is continuously emitted from simple solutions and dry mixes to which it has been added. Various techniques have been developed to hinder or delay the release of the perfume from the composition so that the composition remains aesthetically pleasing for a prolonged length of time. For example, see West German Pat. No. 825,293, Dec. 17, 1951; East German Pat. No. 15,693, Oct. 12, 1975; U.S. Pat. No. 3,772,215, issued Nov. 13, 1973; and U.S. Pat. No. 3,567,119, issued Mar. 2, 1971. While such methods of prolonging the release of perfume from the composition are effective to a limited extent, there is still a need to economically formulate a perfumed particle which continually emits perfume for a substantial length of time.

It will be recognized that a product should desirably have an initial pleasant smell and be capable of delivering that pleasant smell over a long length of time. Encapsulation techniques have a tendency to enclose the perfume so that it is not noticeable until actual use of the product, when the encapsulating material dissolves and the perfume is released. Such techniques are generally also expensive. Other techniques, such as absorption techniques, of "fixing" perfumes have the disadvantage of generally low perfume loads and high perfume losses during manufacture. It is desirable in detergent composition usage that the product have a pleasant smell while in storage and provide strong fragrance impact upon addition to water. My recent U.S. Pat. No. 4,209,417 provided a solution to these requirements in the form of heavily perfumed particles having both immediate and long lasting perfume emitting properties consisting essentially of from 30% to 70% water-insoluble perfume, from 25% to 65% of a water-soluble polymer, and emulsifier. The particles were comprised of a continuous polymer matrix having dispersed substantially uniformly therethrough perfume/emulsifier droplets. Those perfume particles were taught to be prepared by forming an aqueous dispersion consisting essentially of from 2% to 40% perfume, from 5 to 20% water-soluble polymer, from 40 to 90% water, and sufficient emulsifier to form a stable emulsion of the perfume in the water-soluble polymer solution. The aqueous dispersion was cast upon a surface for drying and dried to form a film. The film was comminuted to form particles of the desired size for use in detergent compositions.

The drying step of this process is disadvantageous in that it is energy-expensive, time consuming, and adds nothing, other than dry, granular form, to the finished product.

It is an object of this invention to formulate a perfumed particle having a high level of perfume and having the capability of emitting perfume over a prolonged time period.

It is another object of this invention to provide a perfumed particle which gives an immediate and long lasting perfume effect and additionally releases perfume upon contact with water.

It is yet another object of this invention to provide such heavily perfumed particles which additionally contain other hydratable materials useful in detergent compositions.

A still further object of this invention is to provide a strongly perfumed particle containing a hydratable material useful in detergent compositions which can be made by a process which does not require a separate drying step.

It is another object of this invention to formulate a detergent composition containing perfume particles, such that the detergent composition emits perfume for a substantial length of time during storage and, thereafter, upon contact with water, emits perfume strongly.

DISCLOSURE OF THE INVENTION

In this invention, an emulsion of perfume in an aqueous solution of water-soluble polymer is mixed with a powdered, anhydrous, hydratable material, useful in detergent compositions, in such a ratio that all of the water in the emulsion can be held as the hydrate of the material. Thus, a separate drying step is unnecessary.

In making the compositions of this invention, two materials will be prepared and mixed. One will be a liquid, the perfume/water/emulsifier emulsion. In this emulsion, the ingredients can have the same relative proportions as disclosed in my U.S. Pat. No. 4,209,417, which is hereby incorporated herein by reference. In particular, the emulsion will consist essentially of from 2% to 40%, preferably 4% to 25% perfume, from 5% to 20%, preferably 10% to 15% water soluble polymer, from 40% to 90%, preferably 60% to 85% water, and sufficient emulsifier, preferably 0.1% to 3%, to form a stable emulsion of the perfume in the water-soluble polymer solution. In processing, the first step will involve forming an emulsion of the perfume, emulsifier, and polymer in water. Next, this emulsion will preferably be chilled, preferably to a temperature of about 0° C. or below. Finally, the emulsion is mixed with a powdered hydratable material, in such a manner that substantially all of the free water is taken up to form the hydrate of the added material. The resulting particles will consist essentially of from about 0.5% to about 40% water-insoluble perfume, from about 1.5% to about 20% of a water-soluble polymer which will dissolve in water at a temperature of less than 100° C., from about 0.01% to about 5% of an emulsifier, from about 10% to about 90% water, and from about 1.5% to about 75% by weight of a hydratable material, the amount of the hydratable material being sufficient to hold at least about 85% of the water in said particles when fully hydrated. The granular material can be used as is, or can be further comminuted or agglomerated to achieve a desired particle size. The perfumed particles of this invention desirably have an ultimate particle size of from 40 microns to 1400 microns, preferably 175 microns to 1000 microns. The perfume/emulsifier droplets contained within the particles have diameters of from 0.01 microns to 0.5 microns, preferably 0.02 microns to 0.2 microns.

Hydratable Materials

In general, any hydratable material which is either compatible with, or not deleterious to, detergent compositions can be used in the practice of this invention. Such materials include, without limitation, alkali metal halides such as sodium chloride, potassium chloride, sodium fluoride and potassium fluoride. Other hydratable materials include the variety of commonly known detergency builder materials, including polyvalent inorganic or organic salts or mixtures thereof. Examples include alkali metal carbonates, borates, phosphates, polyphosphates, bicarbonates, silicates, and sulfates. Specific examples of such salts include the sodium and potassium tetraborates, perborates, bicarbonates, tripolyphosphates, pyrophosphates, orthophosphates and hexametaphosphates.

Still other materials which may be used as the hydratable materials herein include the commonly used zeolite molecular sieves, also known as zeolites or aluminosilicates. Other, related materials include expandable clays, including sodium and calcium montmorillonites, sodium saponites, and sodium hectorites. The term expandable as used to describe these smectite clays relates to the ability of the layered clay structure to be swollen, or expanded, on contact with water.

In general, the water-soluble polymer and hydratable material employed should be selected so that the hydratable material is more hydrophilic than the water-soluble polymer employed. Since one object of this invention is to produce a dry, free flowing, granular perfume product, excessively hygroscopic or frankly deliquescent materials, which cannot be hydrated to form a stable solid, are to be avoided.

It can also be appreciated that, within the realm of acceptable hydratable materials, those with higher hydration capacities can be used in smaller amounts per volume of emulsion to provide products with higher (wt %) perfume loads, and are therefore preferred.

Regardless of which hydratable material is selected, the amount of hydratable material to be used will be determined by the hydration capacity of the material in relation to the amount of water to be absorbed from the emulsion. In general, it is desirable to have the hydratable material absorb at least about 85% by weight of the water in the emulsion. It can be appreciated that absorption of amounts in excess of 85% of the water will improve the flowability of the resulting product, while adding an amount of hydratable material sufficient to absorb more than 100% of the water will not only insure a free-flowing, granular material, but confer caking resistance to bulk quantities of the perfume particles which result from the practice of this invention.

Thus, for example, sodium tripolyphosphate (STP) is hydratable to form the hexahydrate, i.e., 6 molecules of water are associated with each molecule of STP in the fully hydrated form. Therefore, each mole of STP added to the emulsion in the final processing step will absorb a maximum of 6 moles of water from the emulsion. The actual amount absorbed will be determined by the relative hydrophilicities of the hydratable material and the water-soluble polymer selected. In most cases, complete transfer of water from the polymer solution to the hydratable material will not be achieved, but a dry, granular, free flowing material is produced nonetheless.

The hydration capacity of the hydratable materials used can be determined from standard reference texts, by standard test methods for measuring water of hydration or hydrophilicity, or by simple preparation of test mixtures at various hydration levels and observation of their flowability and propensity for caking. The temperatures of the hydratable material and the polymer/perfume emulsion must be reduced so that the rate of hydration is initially low enough that an intimate mixture of emulsion and hydratable material can be made. If this is not done, large gummy lumps form and it is very difficult to uniformly mix the two components. In general, temperatures near 0° C. allow easy and complete mixing to be effected. The heat of hydration will then help to increase the temperature of the resulting mix to ambient levels.

INDUSTRIAL APPLICABILITY

Perfume

As used herein the term "perfume" is used to indicate any water-insoluble odoriferous material characterized by a vapor pressure below atmospheric pressure at ambient temperatures. The perfume material will most often be liquid at ambient temperatures. A wide variety of chemicals are known for perfume uses, including materials such as aldehydes, ketones and esters. More commonly, naturally occurring plant and animal oils and exudates comprising complex mixtures of various chemical components are known for use as perfumes. The perfumes herein can be relatively simple in their composition or can comprise highly sophisticated complex mixtures of natural and synthetic chemical components, all chosen to provide any desired odor.

Typical perfumes can comprise, for example, woody-/earthy bases containing exotic materials such as sandalwood oil, civet and patchouli oil. The perfumes can be of a light floral fragrance, e.g. rose extract, violet extract, and lilac. The perfumes can also be formulated to provide desirable fruity odors, e.g. lime, lemon and orange. Any chemically compatible material which exudes a pleasant or otherwise desirable odor can be used in the perfumed particles herein.

Water-soluble Polymer

The matrix of the perfumed particles comprises a water-soluble polymer. As used herein, by "water-soluble polymer" is meant a polymer that will dissolve completely in water at a temperature less than 100° C. Any polymer can be used, provided it is water-soluble. Examples include water-soluble polyvinyl alcohols, polyethylene glycols, polyvinyl pyrrolidone, poly(ethylene oxide), cellulose derivatives, e.g. cellulose ethers such as methyl-, ethyl-, propyl- and butylcellulose ether, gelatin, pectin, starches, gum arabic, poly(acrylic acid) and its derivatives, polyacrylamides, styrene maleic anhydrides, poly(vinyl methyl ether maleic anhydrides), amorphous poly(vinyl methyl ether), poly(vinyl 2-methoxyethyl ethers), poly(vinyl sulfonic acid) or its sodium salt, poly(4-vinyl-phthalic acid), and low m.w. melamine formaldehyde resins. Any of the aforementioned polymers which are water-soluble are used herein. Preferred polymers include polyvinyl alcohols, polyethylene glycol, polyvinyl pyrrolidones, cellulose derivatives, poly(acrylic acid) and its derivatives, the poly(acrylamides) and poly(ethylene oxides), and poly(-methyl vinyl ether/maleic anhydride) co-polymers.

Most preferred for use herein are the poly(methyl vinyl ether maleic anhydride) co-polymers.

Emulsifier

The emulsifier is used to emulsify the perfume into an aqueous solution of the water-soluble polymer. The perfume, as used at the high levels of this invention, and the water-soluble polymer are not miscible. Processing to form homogeneous particles would not be possible since phase separation of the two components would occur. However, use of an emulsifier causes the perfume to form droplets which are uniformly distributed throughout the polymer solution. The distribution of perfume/emulsifier droplets allows for a heavy loading of perfume in the particles. The emulsifier is used in an amount sufficient to emulsify the perfume in the aqueous solution of the water-soluble polymer. This amount can vary widely depending on the particular perfume, water-soluble polymer and particular emulsifiers.

Emulsifiers are of a nonionic, anionic or cationic nature. Examples of satisfactory nonionic emulsifiers include fatty alcohols having 10 to 20 carbon atoms condensed with 2 to 20 moles of ethylene oxide and or propylene oxide; alkyl phenols with 6 to 12 carbon atoms in the alkyl chain, condensed with 2 to 20 moles of ethylene oxide, mono- and di-fatty acid esters of ethylene glycol, wherein the fatty acid moiety contains from 10 to 20 carbon atoms; fatty acid monoglycerides, wherein the fatty acid moiety contains from 10 to 20 carbon atoms; sorbitan esters; polyoxyethylene sorbitol; polyoxyethylene sorbitan; and hydrophilic wax esters. Suitable anionic emulsifiers include the fatty acid soaps, e.g. sodium, potassium and triethanolamine soaps, wherein the fatty acid moiety contains from 10 to 20 carbon atoms. Other suitable anionic emulsifiers include the alkali metal, ammonium or substituted ammonium alkyl sulfates, alkyl arylsulfonates, and alkyl ethoxy ether sulfonates having 10 to 30 carbon atoms in the alkyl moiety. The alkyl ethoxy ether sulfonates contain from 1 to 50 ethylene oxide units. Satisfactory cationic emulsifiers are the common quaternary ammonium, morpholinium and pyridinium compounds.

Optional Components

Optional components such as dyes, antioxidants, etc. can be included as a part of the perfumed particles in minor amounts.

Detergent Compositions

The perfumed particles described above are especially useful when included as part of a detergent composition. The detergent composition contains a water-soluble organic surfactant and other detergency adjunct materials in addition to the perfumed particles. The level of surfactant depends upon the type of detergency product, but generally ranges from 0.05% to 35%. The organic surfactants are selected from the group consisting of anionic surfactants, nonionic surfactants, ampholytic surfactants, zwitterionic surfactants, and mixtures thereof. U.S. Pat. No. 3,664,961, issued May 23, 1972, the disclosures of which are fully incorporated herein by reference, describes suitable surfactants. The detergent composition can be a pre-soak detergent composition, main wash detergent composition, or household cleaner detergent composition and can be prepared in any suitable solid granular or powder form. Pre-soak and household cleaner detergent compositions contain a low level of surfactant, primarily for dispersing the composition throughout the aqueous bath. A level of surfactant from 0.05% to 2%, preferably 0.25% to 1% is used. A main wash detergent composition contains from 5% to 35%, preferably 8% to 20% surfactant.

The balance of the detergent composition consists essentially of a detergency adjunct material. The detergency adjunct materials include builders, soil suspending agents, processing aids, brighteners, enzymes, and bleaches. The particular nature of the adjunct materials is dependent on the use of the product. A preferred detergent composition is a built detergent composition containing from 10% to 80%, preferably 25% to 75% detergency builder. Any of the known compounds possessing builder properties are useful herein. U.S. Pat. No. 3,664,961 also describes satisfactory detergency builders. Many of these detergency builders, in particular, sodium tripolyphosphate, are particularly useful as the hydratable materials in the perfumed particles of this invention. Thus, the perfumed particles of this invention can supply a small proportion of the detergency builder in the total detergent composition.

To provide appropriate levels of fragrance, the detergent compositions herein comprise from about 0.1% to 1%, preferably 0.2% to 0.5% of the perfumed particles. The balance of the composition comprises surfactant and detergency adjunct materials as described above.

Detergent compositions containing the above described perfume particles possess a pleasant smell immediately after manufacture, and also after storage for a substantial period. In addition, when the detergent composition is ultimately used in an aqueous solution an additional burst of perfume is released. That is, as the particles dissolve in water, additional perfume entrapped within the polymeric matrix is released. Thus, a slight but noticeable perfume effect is obtained during storage while a stronger perfume effect is noticed upon use of the detergent composition.

The following examples are illustrative of the invention, while not intending to be of limitative thereof.

EXAMPLE I

An aqueous solution is made containing 25.0 g polyvinyl alcohol (PVA) (M.W.=90,000; 98.8% hydrolyzed), 0.5 g ditallow dimethyl ammonium chloride (DTDMAC) (as the emulsifier) and 225.0 gm water. The solution is put into a blender and agitated until the PVA is dissolved. The solution is then deaerated and cooled. Mixing is resumed and 25.0 gm of Cedar Pine perfume is added to the vortex of the agitated solution. The mixture is agitated vigorously for about 1 minute and again deaerated. The resulting emulsion is cooled to about 0° C. At the same time, 776 g of anhydrous sodium tripolyphosphate (STP) are also cooled to about 0° C. The emulsion and STP are mixed together at moderate shear and gradually allowed to warm to ambient temperature during mixing. The resulting product is a dry, free-flowing, granular material having a mild fragrance. The average analysis is:

PVA 2.4%
DTDMAC .05%
$H_2O$ 21.4%
Perfume 2.4%
STP 74%

EXAMPLE II 13 grams of Gantrez AN 139 poly(Methyl vinyl ether/maleic anhydride) are dissolved in 67 grams $H_2O$.

The solution is heated to hydrolyze the anhydride groups and 1.42 g of Atlas G-1702 (polyoxyethylene sorbitol beeswax derivative) and 1.42 g Myrj 45 (polyoxyethylene (8) stearate) are added as emulsifiers. To this mixture is added 13 grams "Bloom" perfume, and a stable emulsion is formed by high shear mixing. After emulsification, 1 gram of $Ca(OH)_2$ is added to crosslink the polymer chains for better perfume retention. The emulsion is deaerated and cooled to below 0° C. using pulverized dry ice. The frozen particles of emulsion are mixed with 117 grams of similarly cooled anhydrous sodium sulfate at moderate shear and the entire batch is allowed to warm to ambient temperature during mixing. The resulting product is a dry, free-flowing, granular material.

Another "control" batch is made as above, but without the Gantrez AN 139. Samples of each batch are placed in open Petri dishes and exposed to ambient conditions. After 1 week, little fragrance is detectable over either sample. Upon addition of $H_2O$, "Bloom" fragrance is strongly emitted from the sample containing the Gantrez polymer, none is detectable over the control sample.

EXAMPLE III

A household cleaning composition is formulated as follows:

Sodium sesquicarbonate: 63.8%
Sodium $C_{12}$ alkyl benzene sulfonate: 0.9%
Tail oil ethoxylated with an average of 8 moles ethylene oxide: 0.1%
Trisodium phosphate: 10.0%
Sodium tripolyphosphate: 22.1%
Perfumed particles of Example II: 2.1%
Misc. (coloring matter and water): 0.1%

The composition has a pleasant odor during storage and when made into an aqueous solution prior to use (15 gm product per liter water) emits a strong but pleasing perfume smell.

All percentages herein are by weight, unless otherwise indicated.

What is claimed is:

1. Heavily perfumed particles having both immediate and long lasting perfume emitting properties, consisting essentially of from about 0.5% to about 40% water-insoluble perfume, from about 1.5% to about 20% of a water-soluble polymer which will dissolve in water at a temperature of less than 100° C., from about 0.01% to about 5% of an emulsifier, from about 10% to about 90% water, and from about 1.5% to about 75% by weight of a hydratable material, the amount of the hydratable material being sufficient to hold at least about 85% of the water is said particles when fully hydrated.

2. Particles according to claim 1 wherein the water soluble polymer is a member selected from the group consisting of:
poly(methyl vinyl ether/maleic anhydride),
poly(ethylene oxides),
poly(acrylamides),
poly(acrylic acid),
polyvinyl pyrrolidones,
polyethylene glycols,
cellulose derivatives,
polyvinyl alcohols, and
poly(acrylic acid) derivatives.

3. Particles according to claim 2 wherein the water soluble polymer is poly(methyl vinyl ether/maleic anhydride).

4. Particles according to claim 1 wherein the hydratable material is a member selected from the group consisting of:
alkali metal halides,
alkali metal carbonates,
alkali metal silicates,
alkali metal sulfates,
alkali metal borates,
alkali metal phosphates,
alkali metal polyphosphates,
alkali metal bicarbonates,
zeolite molecular sieves, and expandable smectite clays.

5. Particles according to claim 4 wherein the hydratable material is sodium tripolyphosphate.

6. Particles according to claim 4 wherein the hydratable material is a zeolite molecular sieve material having, in the anhydrous state, a hydration capacity of from about 15 to about 30 grams of water per gram of material.

7. A process for producing heavily perfumed particles having both immediate and long lasting perfume emitting properties comprising the steps of
(a) forming an aqueous dispersion consisting essentially of from 2% to 40% of a water-insoluble perfume, from 5% to 20% of a water-soluble polymer which will dissolve in water at a temperature of less than 100° C., from 40% to 90% water, and sufficient emulsifier to emulsify the perfume in the dispersion;
(b) cooling the dispersion of step (a) to about 0° C. or less;
(c) mixing the cooled dispersion of step (b) with an amount of anhydrous, hydratable material sufficient to hold at least about 85% of the water in the dispersion when fully hydrated; and
(d) warming the mixture of step (c), while mixing, to ambient temperature.

8. A process according to claim 7 wherein the dispersion is cooled without freezing the dispersion.

9. A process according to claim 7 wherein the dispersion is cooled to below its freezing point and which further comprises the step of comminuting the frozen dispersion prior to mixing with the anhydrous hydratable material.

10. A process according to claim 7 which further comprises the step of cooling the anhydrous hydratable material to about 0° C. or less prior to mixing with the aqueous dispersion.

11. A process according to claim 7 wherein the water soluble polymer is a member selected from the group consisting of:
poly(methyl vinyl ether/maleic anhydride),
poly(ethylene oxides),
poly(acrylamides),
poly(acrylic acid),
poly vinyl pyrrolidones,
polyethylene glycols,
cellulose derivatives,
polyvinyl alcohols, and
poly(acrylic acid) derivatives.

12. A process according to claim 7 wherein the hydratable material is a member selected from the group consisting of:
alkali metal halides,
alkali metal carbonates,
alkali metal silicates,
alkali metal sulfates,
alkali metal borates,
alkali metal phosphates,
alkali metal polyphosphates,
alkali metal bicarbonates,
zeolite molecular sieves, and expandable smectite clays.

* * * * *